(12) United States Patent
Randolph et al.

(10) Patent No.: US 7,906,700 B2
(45) Date of Patent: Mar. 15, 2011

(54) ALKYLATION OF ISOBUTENE FEEDS

(75) Inventors: Bruce B. Randolph, Bartlesville, OK (US); Keith W. Hovis, Stillwater, OK (US); Kenneth C. Hoover, New Hartford, NY (US)

(73) Assignee: UOP LLC, Des Plaines, IL (US)

( * ) Notice: Subject to any disclaimer, the term of this patent is extended or adjusted under 35 U.S.C. 154(b) by 886 days.

(21) Appl. No.: 11/445,354

(22) Filed: Jun. 1, 2006

(65) Prior Publication Data

US 2007/0282150 A1 Dec. 6, 2007

(51) Int. Cl.
*C07C 2/00* (2006.01)

(52) U.S. Cl. ......... 585/709; 208/134; 208/141; 585/723; 585/730; 585/731

(58) Field of Classification Search .................. 585/709, 585/724, 730–731; 208/134, 141
See application file for complete search history.

(56) References Cited

U.S. PATENT DOCUMENTS

| | | | | |
|---|---|---|---|---|
| 3,435,092 A * | 3/1969 | Hutson, Jr. et al. | ............ | 585/720 |
| 3,761,540 A | 9/1973 | Hutson, Jr. et al. | ...... | 260/683.51 |
| 4,049,728 A | 9/1977 | Kraus et al. | ................. | 260/653.6 |
| 4,199,409 A | 4/1980 | Skraba | ............................ | 203/39 |
| 4,205,196 A | 5/1980 | Makovec et al. | ............... | 585/701 |
| 4,207,423 A | 6/1980 | Makovec et al. | ............... | 585/332 |
| 4,236,036 A | 11/1980 | Dixon et al. | ................... | 585/331 |
| 4,276,257 A | 6/1981 | Dixon et al. | ..................... | 422/62 |
| 4,276,439 A | 6/1981 | Hutson, Jr. et al. | ............ | 585/720 |
| 4,304,947 A | 12/1981 | Hutson, Jr. | ..................... | 585/301 |
| 4,317,795 A | 3/1982 | Makovec et al. | ................. | 422/62 |
| 4,383,977 A | 5/1983 | Hutson, Jr. et al. | ............ | 422/235 |
| 4,500,490 A | 2/1985 | Hutson, Jr. | ...................... | 422/62 |
| 5,639,932 A * | 6/1997 | Abbott et al. | .................. | 585/724 |
| 5,792,896 A | 8/1998 | Randolph et al. | ............. | 585/724 |
| 6,995,296 B2 | 2/2006 | Smith, Jr. et al. | | |
| 2004/0077910 A1 | 4/2004 | Podrebarac et al. | | |

OTHER PUBLICATIONS

Pacek, A.W. et al. (1998). Chemical Engineering Science, 53(11), 2005-2011.*
Esteves, P.M. et al. (2005). Journal of Physical Chemistry B, 109(26), 12946-12955.*
Chaput et al., "Pretreat alkylation feed", Hydrocarbon Processing, Sep. 1992, pp. 51-54.

* cited by examiner

*Primary Examiner* — Robert J Hill, Jr.
*Assistant Examiner* — Brian McCaig
(74) *Attorney, Agent, or Firm* — James C Paschall

(57) ABSTRACT

A process for alkylating isobutene by introducing a feed containing isobutene and an isoparaffin, in the form of droplets, into an acid catalyst to produce an alkylation product, wherein the Sauter mean diameter of the droplets is greater than or equal to about 150 μm and is less than or equal to about 500 μm, is disclosed.

32 Claims, No Drawings

ALKYLATION OF ISOBUTENE FEEDS

The present invention relates to a method and/or system for the alkylation of an isobutene feed with an isoparaffin utilizing an acidic catalyst mixture. In another aspect, this invention relates to a method of improving the quality of alkylate produced from isobutene feeds by controlling the hydrocarbon feed droplet sizes.

The use of catalytic alkylation processes to produce branched hydrocarbons having properties that are suitable for use as gasoline blending components is well known in the art. Generally, the alkylation of olefins by saturated hydrocarbons, such as isoparaffins, is accomplished by contacting the reactants with an acid catalyst to form a reaction mixture, settling the reaction mixture to separate the catalyst from the hydrocarbons, thereby forming a catalyst phase and a hydrocarbon phase. The hydrocarbon phase is further separated, for example, by fractionation, to recover the separate product streams. Normally, the hydrocarbon phase of the alkylation process contains hydrocarbons having five to ten carbon atoms per molecule. In order to have the highest quality gasoline blending stock, it is preferred for the alkylate hydrocarbons formed in the alkylation process to be highly branched and contain seven to nine carbon atoms per molecule.

Future motor fuel regulations are expected to continue the trend of reducing the volumes of hydrocarbons containing four or five carbon atoms per molecule in gasoline. In addition, the probable elimination of MTBE from gasoline creates several new issues regarding composition. One such issue is the reduction in octane when MTBE is removed. MTBE has a good octane rating ((R+M)/2 of ~110), a low vapor pressure (~8.5 Rvp) and good distillation characteristics from a Driveability Index viewpoint. Another issue is the increase in isobutene availability, which would have been used to make MTBE, for alkylation or oligomerization. Although isobutene-containing feeds can produce high octane alkylate with hydrofluoric acid containing catalysts, the on-purpose alkylation of isobutene feeds presents some challenges. The major issues with isobutene feeds are the oligomerization/β-scission reactions. Isobutene is easily oligomerized under typical alkylation reaction conditions, and the resultant alkylate can have higher levels of $C_9+$ hydrocarbons (heavy alkylate derived from the oligomers), increased $iC_5$-$C_7$ hydrocarbon products (via β-scission of the oligomer) and poor overall quality (high T90, high endpoint and low octane).

We have discovered that controlling the droplet size distribution with isobutene feeds is critical to forming high quality alkylate, and that this droplet size effect is unexpectedly much more pronounced for predominantly isobutene feeds than for mixed olefin feeds of propene, isobutene, 1-butene, 2-butene and pentenes.

BRIEF SUMMARY OF THE INVENTION

It is, thus, an object of the present invention to provide an improved process for alkylating isobutene.

A further object of this invention is to provide a process for improving the quality of alkylate produced from isobutene feeds by controlling the hydrocarbon feed droplet sizes.

In accordance with one embodiment of the present invention, a process is provided including:
introducing a feed comprising isobutene and an isoparaffin and absent sufficient non-isobutene olefins which negatively impact the alkylate quality of alkylation product produced, in the form of droplets, into an acid catalyst to thereby produce the alkylation product, wherein the Sauter mean diameter of the droplets is greater than or equal to about 150 μm and is less than or equal to about 500 μm, and wherein the concentration of hydrocarbons having equal to or greater than nine carbon atoms per molecule in the alkylation product is less than the concentration of hydrocarbons having equal to or greater than nine carbon atoms per molecule in an alkylation product produced in a process wherein the Sauter mean diameter is greater than about 500 μm.

In accordance with another embodiment of the present invention, a process is provided including:
introducing a feed comprising an olefin and an isoparaffin, in the form of droplets, into an acid catalyst to thereby produce an alkylation product, wherein the olefin comprises at least about 50 wt. % isobutene and wherein the Sauter mean diameter of the droplets is greater than or equal to about 150 μm and is less than or equal to about 500 μm, and wherein the concentration of hydrocarbons having equal to or greater than nine carbon atoms per molecule in the alkylation product is less than the concentration of hydrocarbons having equal to or greater than nine carbon atoms per molecule in an alkylation product produced in a process wherein the Sauter mean diameter is greater than about 500 μm.

In accordance with yet another embodiment of the present invention, a process is provided including:
introducing a feed consisting essentially of isobutene and an isoparaffin, in the form of droplets, into an acid catalyst to thereby produce an alkylation product, wherein the Sauter mean diameter of the droplets is greater than or equal to about 150 μm and is less than or equal to about 500 μm, and wherein the concentration of hydrocarbons having equal to or greater than nine carbon atoms per molecule in the alkylation product is less than the concentration of hydrocarbons having equal to or greater than nine carbon atoms per molecule in an alkylation product produced in a process wherein the Sauter mean diameter is greater than about 500 μm.

DETAILED DESCRIPTION OF THE INVENTION

In accordance with one embodiment of the invention, the feed to the process comprises isobutene and an isoparaffin and is absent sufficient non-isobutene olefins which negatively impact the alkylate quality of alkylation product produced.

For the purposes of this invention, negative impacts to alkylate quality of the alkylation product include, but are not limited to, increased $C_9+$ hydrocarbon concentration, increased $C_5$-$C_7$ hydrocarbon products, elevated T90 temperature (temperature at which 90% of the subject alkylation product boils off), elevated end point temperature (temperature at which the heaviest portion of the alkylation product boils off), and lower road octane rating ((R+M)/2).

In accordance with another embodiment of the invention, the feed to the process comprises an olefin and an isoparaffin, wherein the olefin comprises at least about 50 wt. %, more preferably at least about 70 wt. %, and most preferably at least about 90 wt. % isobutene.

In accordance with yet another embodiment of the invention, the feed consists essentially of or consists of isobutene and an isoparaffin.

In each embodiment, the feed is introduced, in the form of droplets, into an acid catalyst to thereby produce an alkylation product. The Sauter mean diameter of the droplets is preferably greater than or equal to about 150 μm and is less than or equal to about 500 μm, more preferably is greater than or equal to about 150 μm and is less than or equal to about 450 μm, and most preferably is greater than or equal to about 150 μm and is less than or equal to about 400 μm.

The concentration of hydrocarbons having equal to or greater than nine carbon atoms per molecule in the alkylation product is less than the concentration of hydrocarbons having equal to or greater than nine carbon atoms per molecule in an alkylation product produced in a process wherein the Sauter mean diameter is greater than about 400 μm, more preferably greater than about 450 μm, and most preferably greater than about 500 μm.

The isoparaffin can be any alkylatable isoparaffin, and is preferably selected from the group consisting of isobutane, isopentane, isohexane, and combinations thereof.

The acid catalyst can be any acid catalyst capable of producing alkylation of an olefin with an isoparaffin.

The catalyst useful in the process can comprise, consist of, or consist essentially of hydrogen fluoride. Alternatively, the catalyst can: 1) comprise, consist of, or consist essentially of hydrogen fluoride and water; or 2) comprise, consist of, or consist essentially of hydrogen fluoride and a volatility reducing additive; or 3) comprise, consist of, or consist essentially of hydrogen fluoride, a volatility reducing additive, and water or comprise, consist of, or consist essentially of sulfuric acid.

The volatility reducing additive can be any compound effective in reducing the volatility of a mixture resulting from the addition of the volatility reducing additive to hydrofluoric acid. More particularly, the volatility reducing additive can be a compound selected from the group consisting of sulfone, ammonia, methylamines, ethylamines, propylamines, butylamines, pentylamines, pyridine, alkylpryidines, melamine, hexamethylene-tetramine and the like, and combinations of any two or more thereof.

The sulfones suitable for use in this invention are the sulfones of the general formula $$R\text{—}SO_2\text{—}R^1$$

wherein R and $R^1$ are monovalent hydrocarbon alkyl or aryl substituents, each containing from 1 to 8 carbon atoms, and wherein R and $R^1$ can be the same or different. Examples of suitable sulfones include, but are not limited to, dimethylsulfone, di-n-propylsulfone, diphenylsulfone, ethylmethylsulfone and alicyclic sulfones wherein the $SO_2$ group is bonded to a hydrocarbon ring. In such a case, R and $R^1$ are forming together a branched or unbranched hydrocarbon divalent moiety preferably containing from 3 to 12 carbon atoms. Among the latter, tetramethylenesulfone or sulfolane, 3-methylsulfolane and 2,4-dimethylsulfolane are more particularly suitable since they offer the advantage of being liquid at process operating conditions of concern herein. These sulfones may also have substituents, particularly one or more halogen atoms, such as for example, chloromethylethylsulfone. These sulfones may advantageously be used in the form of mixtures of any two or more thereof. The most preferred volatility reducing additive is sulfolane.

The following example is provided to further illustrate this invention and is not to be considered as unduly limiting the scope of this invention.

EXAMPLE

The feeds in these runs included an olefin feed component and an isoparaffin feed component. The olefin feed component was either a 99.5 wt. % pure grade isobutene sample from a commercial supplier or a mixed olefin feed containing 25.1 wt. % propene, 19.9 wt. % isobutylene, 16.9 wt. % 1-butene, 34.8 wt. % 2-butene, and 3.3 wt. % pentenes. The isoparaffin feed component contained 98.5 wt. % isobutane and 1.5 wt. % propane and n-butane.

The reactor(s) used were one inch diameter Monel® schedule 40 pipe 24 inches in length. The diameter of the feed nozzles used was 0.020 inch with a 0° spray angle. The acid phase was a 99% hydrogen fluoride/1% water blend, circulated with a magnetically driven gear pump. All Runs were conducted at ~95° F. For each Run, the hydrocarbon feed was passed up through the nozzle, creating droplets, which then passed through the 24 inch layer of acid phase whereupon samples of the treated hydrocarbons were collected and analyzed by gas chromatography (GC).

The results for each Run are presented in the Table below.

TABLE

| | Run | | | |
|---|---|---|---|---|
| | A | B | C | D |
| Olefin Feed | Isobutene | Isobutene | Mixed Olefin | Mixed Olefin |
| Feed Rate, mL/hr | 347 | 258 | 368 | 241 |
| Estimated Droplet Sauter Mean Diameter (SMD), μm[1] | ~350 | ~900 | ~350 | ~900 |
| Product Component wt.% | | | | |
| Isopentane | 5.71 | 8.79 | 5.78 | 6.64 |
| N-pentane | 0 | 0 | 0.07 | 0.09 |
| Hexane | 3.31 | 4.64 | 4.56 | 4.66 |
| Heptane | 3.75 | 4.36 | 17.6 | 17.7 |
| Octane | 73.4 | 57.0 | 55.4 | 56.8 |
| $C_9$+ | 13.8 | 25.2 | 16.5 | 14.1 |
| Trimethylpentane (TMP) | 64.4 | 48.3 | 46.0 | 47.5 |
| Dimethylhexane (DMH) | 8.55 | 8.23 | 9.01 | 8.87 |
| RON (estimated)[2] | 93.9 | 91.4 | 91.6 | 91.9 |
| MON (estimated)[2] | 93.0 | 90.8 | 90.6 | 90.8 |
| T90 (estimated)[2] | 273 | 306 | 281 | 274 |
| End Point (estimated)[2] | 396 | 429 | 403 | 397 |

[1] SMD was estimated using correlations developed from literature sources relating velocity, interfacial tension, density and temperature to droplet size. This requires using proprietary thermodynamic data for HF/hydrocarbon systems.
[2] Estimated from the pure component values, per Hutson and Logan, Hydrocarbon Processing, 1975, Vol. 54, #9, p. 107–110.

As can be seen from the data in the Table, controlling the droplet size (in the case of the example by varying the Feed Rate) to an estimated SME less than 500 μm in Run A resulted in significant improvements in alkylate quality as compared to the ~900 μm SMD in Run B. More particularly, the concentration of TMP (favored component of alkylate) increased substantially in Run A over Run B, and the RON, MON, T90 and End Point values were also significantly better for Run A as compared to Run B.

As also can be seen from the data in the Table, this same improvement in alkylate quality was not observed for the mixed olefin feed as between Runs C and D. In fact, with regard to the above mentioned alkylate quality indicators (TMP concentration, RON, MON, T90 and End Point), the alkylate product produced in Run D, which saw droplets having a SMD of ~900 μm, was slightly better than the alkylate produced in Run C, which saw droplets having a SMD of ~350 μm.

While this invention has been described in detail for the purpose of illustration, it should not be construed as limited thereby but intended to cover all changes and modifications within the spirit and scope thereof.

That which is claimed is:

1. A process for improving alkylate quality of alkylation product, comprising introducing a feed comprising isobutene and an isoparaffin and absent sufficient non-isobutene olefins which negatively impact the alkylate quality of alkylation product produced such that isobutene comprises at least 50 wt-% of the olefin in the feed, in the form of droplets, into an acid catalyst to thereby produce said alkylation product, wherein the Sauter mean diameter of said droplets is greater than or equal to about 150 µm and is less than or equal to about 500 µm, and wherein:
  (i) the concentration of hydrocarbons having equal to or greater than nine carbon atoms per molecule in said alkylation product is less than the concentration of hydrocarbons having equal to or greater than nine carbon atoms per molecule in, and
  (ii) the road octane rating ((R+M)/2) of said alkylation product is higher than that of,
  an alkylation product produced in a process wherein the Sauter mean diameter is greater than about 500 µm.

2. A process as recited in claim 1 wherein the Sauter mean diameter of said droplets is greater than or equal to about 150 µm and is less than or equal to about 450 µm.

3. A process as recited in claim 1 wherein the Sauter mean diameter of said droplets is greater than or equal to about 150 µm and is less than or equal to about 400 µm.

4. A process as recited in claim 1 wherein said isoparaffin is selected from the group consisting of isobutane, isopentane, isohexane, and combinations thereof.

5. A process as recited in claim 1 wherein said acid catalyst comprises an acid selected from the group consisting of hydrofluoric acid and sulfuric acid.

6. A process as recited in claim 1 wherein said acid catalyst comprises hydrofluoric acid.

7. A process as recited in claim 1 wherein said acid catalyst comprises hydrofluoric acid and a volatility reducing additive.

8. A process as recited in claim 7 wherein said volatility reducing additive comprises a sulfone.

9. A process as recited in claim 7 wherein said volatility reducing additive comprises sulfolane.

10. A process as recited in claim 1 wherein said acid catalyst comprises sulfuric acid.

11. A process for improving alkylate quality of alkylation product, comprising introducing a feed comprising an olefin and an isoparaffin, in the form of droplets, into an acid catalyst to thereby produce an alkylation product, wherein said olefin comprises at least about 50 wt.% isobutene and wherein the Sauter mean diameter of said droplets is greater than or equal to about 150 µm and is less than or equal to about 500 µm, and wherein:
  (i) the concentration of hydrocarbons having equal to or greater than nine carbon atoms per molecule in said alkylation product is less than the concentration of hydrocarbons having equal to or greater than nine carbon atoms per molecule in, and
  (ii) the road octane rating ((R+M)/2) of said alkylation product is higher than that of,
  an alkylation product produced in a process wherein the Sauter mean diameter is greater than about 500 µm.

12. A process as recited in claim 11 wherein the Sauter mean diameter of said droplets is greater than or equal to about 150 µm and is less than or equal to about 450 µm.

13. A process as recited in claim 11 wherein the Sauter mean diameter of said droplets is greater than or equal to about 150 µm and is less than or equal to about 400 µm.

14. A process as recited in claim 11 wherein said olefin comprises at least about 70 wt.% isobutene.

15. A process as recited in claim 11 wherein said olefin comprises at least about 90 wt.% isobutene.

16. A process as recited in claim 11 wherein said isoparaffin is selected from the group consisting of isobutane, isopentane, isohexane, and combinations thereof.

17. A process as recited in claim 11 wherein said acid catalyst comprises an acid selected from the group consisting of hydrofluoric acid and sulfuric acid.

18. A process as recited in claim 11 wherein said acid catalyst comprises hydrofluoric acid.

19. A process as recited in claim 11 wherein said acid catalyst comprises sulfuric acid.

20. A process as recited in claim 11 wherein said acid catalyst comprises hydrofluoric acid and a volatility reducing additive.

21. A process as recited in claim 20 wherein said volatility reducing additive comprises a sulfone.

22. A process as recited in claim 20 wherein said volatility reducing additive comprises sulfolane.

23. A process for improving alkylate quality of alkylation product, comprising introducing a feed consisting essentially of isobutene and an isoparaffin, in the form of droplets, into an acid catalyst to thereby produce an alkylation product, wherein the Sauter mean diameter of said droplets is greater than or equal to about 150 µm and is less than or equal to about 500 µm, and wherein:
  (i) the concentration of hydrocarbons having equal to or greater than nine carbon atoms per molecule in said alkylation product is less than the concentration of hydrocarbons having equal to or greater than nine carbon atoms per molecule in, and
  (ii) the road octane rating ((R+M)/2) of said alkylation product is higher than that of,
  an alkylation product produced in a process wherein the Sauter mean diameter is greater than about 500 µm.

24. A process as recited in claim 23 wherein the Sauter mean diameter of said droplets is greater than or equal to about 150 µm and is less than or equal to about 450 µm.

25. A process as recited in claim 23 wherein the Sauter mean diameter of said droplets is greater than or equal to about 150 µm and is less than or equal to about 400 µm.

26. A process as recited in claim 23 wherein said isoparaffin is selected from the group consisting of isobutane, isopentane, isohexane, and combinations thereof.

27. A process as recited in claim 23 wherein said acid catalyst comprises an acid selected from the group consisting of hydrofluoric acid and sulfuric acid.

28. A process as recited in claim 23 wherein said acid catalyst comprises hydrofluoric acid.

29. A process as recited in claim 23 wherein said acid catalyst comprises hydrofluoric acid and a volatility reducing additive.

30. A process as recited in claim 29 wherein said volatility reducing additive comprises a sulfone.

31. A process as recited in claim 29 wherein said volatility reducing additive comprises sulfolane.

32. A process as recited in claim 23 wherein said acid catalyst comprises sulfuric acid.

* * * * *